(12) United States Patent
Barnes et al.

(10) Patent No.: US 6,403,341 B1
(45) Date of Patent: Jun. 11, 2002

(54) MAGNESIUM PRECIPITATE HOT START METHOD FOR PCR

(75) Inventors: Wayne M. Barnes, 11 Princeton Ave., University City, MO (US) 63130; Katherine R. Rowlyk, St. Louis, MO (US)

(73) Assignee: Wayne M. Barnes, University City, MO (US)

( * ) Notice: Subject to any disclaimer, the term of this patent is extended or adjusted under 35 U.S.C. 154(b) by 0 days.

(21) Appl. No.: 09/920,872

(22) Filed: Aug. 2, 2001

(51) Int. Cl.$^7$ .......................... C12P 19/34; C07H 21/02; C07H 21/04

(52) U.S. Cl. .................... 435/91.2; 536/23.1; 536/24.33

(58) Field of Search ........................ 435/91.2; 536/23.1, 536/24.33

(56) References Cited

U.S. PATENT DOCUMENTS

| | | | | |
|---|---|---|---|---|
| 4,554,101 A | 11/1985 | Hopp et al. | ............... | 260/112.5 |
| 4,683,195 A | 7/1987 | Mullis et al. | .................. | 435/6 |
| 4,683,202 A | 7/1987 | Mullis | .......................... | 435/91 |
| 5,411,876 A | 5/1995 | Bloch et al. | ................ | 435/91.2 |
| 5,436,149 A | 7/1995 | Barnes | ........................ | 435/194 |
| 5,599,660 A | 2/1997 | Ramanujam et al. | .......... | 435/4 |
| 5,616,494 A | 4/1997 | Barnes | ..................... | 435/252.3 |

OTHER PUBLICATIONS

Barnes WM; "The Fidelity Of Taq polymerase Catalyzing PCR Is Iimproved By An N–terminal Deletion"; *Gene*; vol. 112; pp. 29–25 ; 1992.

Barnes WM; "PCR Amplification Of Up To 35–kb DNA With High Fidelity And High Yield From λ Bacteriophage Templates"; *Proc. Natl. Acad. Sci. USA*; vol. 91; pp. 2216–2220; 1994.

Caldwell, et al.; "Randomization of Genes by PCR Mutagenesis"; PCR Methods Applic.; vol. 2; pp. 28–33; 1992.

Chou Q, Russell M, Birch DE, Raymond J, Bloch W; "Prevention Of Pre–PCR Mis–priming And Primer Dimerization Improves Low–copy–number Amplifications"; *Nucleic Acids Res.*; vol. 20; No. 7; pp. 1717–1723; 1992.

Erlich HA, Gelfand D, Sninsky JJ; "Recent Advances In The Polymerase Chain Reaction"; *Science*; vol. 252; No. 5013; pp. 1643–1651; 1991.

Handyside AH, Kontogianni EH, Hardy K, Winston RM; "Pregnancies From Biopsied Human Preimplantation Embryos Sexed By Y–specific DNA Amplification"; *Nature*; vol. 344; pp. 768–770; 1990.

Herbert B, Bergeron J, Potworowski E and Tijssen P; "Increased PCR Sensitivity By Using Paraffin Wax As A Reaction Mix Overlay"; *Mol. Cell Probes*; vol. 7; pp. 249–252; 1993.

Higuchi R; "Recombinant PCR"; *PCR Protocols: A Guide to Methods and Applications*; pp. 177–183; 1990.

Horton RM, Hoppe BL, Conti–Tronconik BM; "Ampli–Grease: "Hot Start" PCR Using Petroleum Jelly"; *Biotechniques*; vol. 16; No. 1; pp. 42–43; 1994.

Kellogg DE, Rybalkin I, Chen S, Mukhamedova N, Vlaski T, Siebert D, Chenchik A; "TaqStart Antibody™: "Hot Start" PCR Facilitated By A Neutralizing Momoclonal Antibody Directed Against Taq DNA Polymerase", *Biotechniques*; vol. 16; No. 6; pp. 1134–1137; 1994.

Kumar R and Barbacid M; "Oncogene Detection At The Single Cell Level"; *Oncogene*; vol. 3; No. 6; pp. 647–651; 1988.

Lawyer FC, Stoffel S, Saiki RK, Myambo K, Drummond R, Gelfand DH; "Isolation, Characterization, And Expression in *Escherichia Coli* Of The DNA Polymerase Gene From *Thermus Aquaticus*"; *J. Biol. Chem.*; vol. 264; No. 11; pp. 6427–6437; 1989.

Leung D, Chen E, Goeddel D; "A Method For Random Mutagenesis Of A Defined DNA Segment Using A Modified Polymerase Chain Reaction"; *Technique*; vol. 1; No. 1; pp. 11–15; 1989.

McCormick F; "The Polymerase Chain Reaction And Cancer Diagnosis"; Cancer Cells; vol. 1; No. 2; pp. 56–61; 1989.

Moretti T, Koons B, and Budowle B; "Enhancement Of PCR Amplification Yield And Specificity Using AmpliTaq Gold™ DNA Polymerase"; *BioTechniques*; vol. 25; No. 4; pp. 716–722; 1998.

Sacramento D, Bourhy H, Tordo N; "PCR Technique As An Alternative Method For Diagnosis And Molecular Epidemiology Of Rabies Virus"; *Mol. Cell Probes*; vol. 5; pp. 229–240; 1991.

Sagner G, Ruger R, Kessler C; "Rapid Filter Assay For The Detection Of DNA Polymerase Activity: Direct Identification Of The Gene For The DNA Polymerase From *Thermus Aquaticus*", *Gene*; vol. 97; pp. 119–123; 1991.

Saiki RK, Gelfand DH, Stoffel S, Scharf SJ, Higuchi R, Horn GT, Mullis KB, Erlich HA; "Primer–directed Enzymatic Amplification of DNA With A Thermostable DNA Polymerase", *Science*; vol. 239; No. 4839; pp. 487–491; 1988.

Scalice ER, Sharkey DJ, & Daiss JL; "Monoclonal Antibodies Prepared Against The DNA Polymerase From *Thermus Aquaticus* Are Potent Inhibitors Of Enzyme Activity"; *Journal of Immun. Methods*; vol. 172; pp. 147–163; 1994.

(List continued on next page.)

*Primary Examiner*—Kenneth R. Horlick
*Assistant Examiner*—Alexander H. Spiegler
(74) *Attorney, Agent, or Firm*—Senniger, Powers, Leavitt & Roedel (57) ABSTRACT

The present invention provides a method of performing hot start PCR reactions. The method is based on sequestration of magnesium ions in the form of a precipitate which renders a DNA polymerase inactive until the appropriate time in the PCR reaction when a certain temperature is reached and the magnesium ions are released from the precipitate. Also provided are kits comprising reagents and instructions for amplifying a target nucleic acid by the magnesium precipitate hot start.

16 Claims, 5 Drawing Sheets

OTHER PUBLICATIONS

Sharkey DJ, Scalice ER, Christy KG, Atwood SM & Daiss JL; "Antibodies As Thermolabile Switches; High Temperature Triggering For The Polymerase Chain Reaction"; *Bio/Technology*; vol. 12; No. 5; pp. 506–509; 1994.

Wages JM Jr, Hamdallah M, Calabro MA, Fowler AK, Oster CN, Redfield RR, Burke DS; "Clinical Performance Of A Polymerase Chain Reaction Testing Algorithm For Diagnosis Of HIV–1 Infection In Peripheral Blood Mononuclear Cells"; *J. Med. Virol.*; vol. 33; pp. 58–63; 1991.

Wernars K, Delfgou E, Soentoro PS, Notermans S; "Successful Approach for Detection of Low Numbers of Enterotoxigenic *Escherichia coli* in Minced Meat by Using the Polymerase Chain Reaction"; *Appl. Env. Microbiol.*; vol. 57; No. 7; pp. 1914–1919; 1991.

Degen et al.; "The Human Tissue Plasminogen Activator Gene"; *J. Biol. Chem.*; 261(15); pp. 6972–6985; 1986.

Ou et al.; "DNA Amplification for Direct Detection of HIV–1 in DNA of Peripheral Blood Mononuclear Cells"; *Science*; 239; pp. 295–297; 1988.

Giovanni, DI et al.; "Real Time Quantitative PCR Detection Of Intact And Infectious *Cryptosporidium parvum* Oocysts For Water Industry Application"; Abstracts of the 100th General Meeting of the American Society For Microbiology; 2000.

Hill and Keasler; "Identification of Foodborne Pathogens by Nucleic Acid Hybridization"; *Int. J. Food Microbiol.*, vol. 12; pp. 67–75; 1991.

Jackson; "The Polymerase Chain Reaction in Transfusion Medicine"; *Transfusion*; vol. 30; pp. 51–57; 1990.

Ailenberg et al.; "Controlled Hot Start and Improved Specificity in Carrying Out PCR Utilizing Touch–Up and Loop Incorporated Primers (TULIPS)"; *Biotechniques*, vol. 29: pp. 1018–1020; (2000).

```
                         SEQUENCE LISTING

<160> NUMBER OF SEQ ID NOS: 6

<210> SEQ ID NO 1
<211> LENGTH: 34
<212> TYPE: DNA
<213> ORGANISM: Homo sapiens

<400> SEQUENCE: 1
ggaagtacag ctcagagttc tgcagcaccc ctgc                              34

<210> SEQ ID NO 2
<211> LENGTH: 34
<212> TYPE: DNA
<213> ORGANISM: Homo sapiens

<400> SEQUENCE: 2
tgggattata gacacgagcc actgcacctg gccc                              34

<210> SEQ ID NO 3
<211> LENGTH: 28
<212> TYPE: DNA
<213> ORGANISM: Human immunodeficiency virus type 1

<400> SEQUENCE: 3
ataatccacc tatcccagta ggagaaat                                     28

<210> SEQ ID NO 4
<211> LENGTH: 28
<212> TYPE: DNA
<213> ORGANISM: Human immunodeficiency virus type 1

<400> SEQUENCE: 4
tttggtcctt gtcttatgtc cagaatgc                                     28

<210> SEQ ID NO 5
<211> LENGTH: 24
<212> TYPE: DNA
<213> ORGANISM: Cryptosporidium parvum

<400> SEQUENCE: 5
tcctctgccg tacaggatct ctta                                         24

<210> SEQ ID NO 6
<211> LENGTH: 26
<212> TYPE: DNA
<213> ORGANISM: Cryptosporidium parvum

<400> SEQUENCE: 6
tgctgctctt accagtactc ttatca                                       26
```

MAGNESIUM PRECIPITATE HOT START METHOD FOR PCR

FIELD OF THE INVENTION

The present invention is directed to a novel method of performing hot start PCR reactions. Furthermore, the present invention relates to achieving a greater specificity of amplification of a target nucleic acid. Also provided in the present invention are reagents and kits for performing magnesium precipitate hot start PCR reactions.

BACKGROUND OF THE INVENTION

PCR is a rapid and simple method for specifically amplifying a target DNA sequence in an exponential manner. Saiki, et al., *Science* 239:487–4391 (1988). Briefly, the method as now commonly practiced utilizes a pair of primers that have nucleotide sequences complementary to the DNA which flanks the target sequence. The primers are mixed with a solution containing the target DNA (the template), a thermostable DNA polymerase and deoxynucleoside triphosphates (dNTPS) for all four deoxynucleotides (adenosine (A), tyrosine (T), cytosine (C) and guanine (G)). The mix is then heated to a temperature sufficient to separate the two complementary strands of DNA. The mix is next cooled to a temperature sufficient to allow the primers to specifically anneal to sequences flanking the gene or sequence of interest. The temperature of the reaction mixture is then optionally reset to the optimum for the thermostable DNA polymerase to allow DNA synthesis (extension) to proceed. The temperature regimen is then repeated to constitute each amplification cycle. Thus, PCR consists of multiple cycles of DNA melting, annealing and extension. Twenty replication cycles can yield up to a million-fold amplification of the target DNA sequence. In some applications a single primer sequence functions to prime at both ends of the target, but this only works efficiently if the primer is not too long in length. In some applications several pairs of primers are employed in a process commonly known as multiplex PCR.

The ability to amplify a target DNA molecule by PCR has applications in various areas of technology e.g., environmental and food microbiology (Wernars et al., *Appl. Env. Microbiol.,* 57:1914–1919 (1991); Hill and Keasler, *Int. J. Food Microbiol.,* 12:67–75 (1991)), clinical microbiology (Wages et al. *J. Med. Virol.,* 33:58–63 (1991); Sacramento et al., *Mol. Cell Probes,* 5:229–240 (1991)), oncology (Kumar and Barbacid, *Oncogene,* 3:647–651 (1988); McCormick, *Cancer Cells,* 1:56–61 (1989)), genetic disease prognosis (Handyside et al., *Nature,* 344:768–770 (1990)), and blood banking and forensics (Jackson, *Transfusion,* 30:51–57 (1990)).

Although significant progress has been made in PCR technology, the amplification of non-target oligonucleotides due to side-reactions, such as mispriming on non-target background DNA, RNA, and/or the primers themselves, still presents a significant problem. This is especially true in diagnostic applications where PCR is carried out in a milieu containing complex background DNA and/or RNA while the target DNA may be present at a very low level down to a single copy (Chou et al., *Nucleic Acid Res.,* 20:1717–1723 (1992)).

The temperature at which Taq DNA polymerase exhibits highest activity is in the range of 62° to 72° C., however, significant activity is also exhibited in the range of 20° to 37° C. As a result, during standard PCR preparation at ambient temperatures, the primers may prime DNA extension at non-specific sequences because the formation of only a few base pairs at the 3'-end of a primer can result in a stable priming complex. The result can be competitive or inhibitory products at the expense of the desired product. As an example of inhibitory product, structures consisting only of primer, sometimes called "primer dimers" are formed by the action of DNA polymerase on primers paired with each other, regardless of the true target template. The probability of undesirable primer-primer interactions increases with the number of primer pairs in the reaction, as with multiplex PCR. Other examples of inhibitory products are "wrong bands" of various length, caused by mispriming on the template DNA. During PCR cycling, these non-specific extension products can compete with the desired target DNA and/or lead to misinterpretation of the assay.

Since these side reactions often occur during standard PCR preparation at ambient temperature, one method for minimizing these side reactions involves "hot start" PCR. Many PCR analyses, particularly the most demanding ones, benefit from a hot start. About 50% of all PCR reactions show improved yield and/or specificity if a hot start is employed, and in some cases a hot start is absolutely critical. These demanding PCR analyses include those which have very low copy numbers of target (such as 1 HIV genome per 10,000 cells), denatured DNA (many DNA extraction procedures include a boiling step, so that the template is single-stranded during reaction setup), or contaminated DNA e.g., DNA from soil or feces and/or DNA containing large amounts of RNA. However, current methods of achieving a hot start are tedious, expensive, and/or have other shortcomings.

Hot start PCR may be accomplished by various physical, chemical, or biochemical methods. In a physical hot start, the DNA polymerase or one or more reaction components that are essential for DNA polymerase activity is not allowed to contact the sample DNA until all the components required for the reaction are at a high temperature. The temperature must be high enough so that not even partial hybridization of the primers can occur at any locations other than the desired template location, in spite of the entire genome of the cell being available for non-specific partial hybridization of the primers. Thus, the temperature must be high enough so that base pairing of the primers cannot occur at template (or contaminating template) locations with less than perfect or near-perfect homology. This safe starting temperature is typically in the range of 50° to 75° C. and typically is about 10° C. hotter than the annealing temperature used in the PCR.

One physical way a hot start can be achieved is by using a wax barrier, such as the method disclosed in U.S. Pat. Nos. 5,599,660 and 5,411,876. See also Hebert et al., *Mol. Cell Probes,* 7:249–252 (1993); Horton et al., *Biotechniques,* 16:42–43 (1994). Using such methods, the PCR reaction is set up in two layers separated by a 1 mm thick layer of paraffin wax which melts at about 56° C. There are several methods which may be used to separate the reaction components into two solutions. For instance, all of the DNA is added, with 1×buffer but no dNTPs and no DNA polymerase enzyme, in a volume of 25 ml. One drop of melted wax is added and the tubes are all heated to 60° C. for one minute to allow the melted wax to form a sealing layer after which the tubes are cooled so the wax solidifies. Then a 25 ml mixture containing 1×buffer, all of the dNTPs, and the enzyme is added to each reaction. Finally, 1 drop of oil is added, to make 4 total layers. As the thermal cycler protocol heats the tubes to the first melting step (approximately 95° C.), the wax melts and floats to mix with the oil layer, and the two aqueous layers mix by convection as the temperature cycles.

One common variation involving the use of a wax barrier is that the reaction components are assembled with no magnesium ions so that the DNA polymerase enzyme is inactive. The magnesium ion encased in a wax bead is then (or initially) added. A further modification of the wax barrier used in PCR reactions is disclosed in the U.S. Pat. No. 5,599,660. Alternatively, at least one biological or chemical reagent needed for PCR is mixed with a wax carrier, resulting in a reagent that is solid at room temperature. Thus, the addition of other PCR reagents does not activate the DNA polymerase due to the fact that one or some of the reagents are sequestered in the wax. However, upon heating or the addition of a solvent, the sequestered reagent(s) is/are released from the carrier wax and allowed to react with other soluble reagents, leading to the initiation of the PCR reaction. After the amplification is complete, the reactions are cooled to ambient temperature. Thus, a problem with these wax methods, however, is that the wax hardens after the completion of the amplification which makes sample recovery extremely tedious, since the wax tends to plug the pipet tips used to remove the sample. This is true even if the samples are reheated to melt the wax. Another potential problem is cross-contamination if tweezers are used to add wax beads, since slight contact between the tweezers and the tube caps can move DNA template between samples before the PCR reactions start. Furthermore, the addition of a wax or a grease layer can negatively affect a PCR reaction since increasing the total mass of the PCR reaction tube decreases the speed with which the contents of the tube approach the targeted temperatures in the thermal cycler.

Another way to implement a hot start PCR is to use DNA polymerase which is inactivated chemically but reversibly, such as AMPLITAQ GOLD™ DNA polymerase. This enzyme preparation, distributed by PE Applied Biosystems, is distributed to users in inactivated form, but is reactivatable by heating. The required reactivation conditions, however, are extremely harsh to the template DNA: ten minutes at 95° C. and at a nominal pH of 8.3 or lower results in reactivation of some 30% of the enzyme which is enough to start the PCR. See Moretti, et al., *Biotechniques* 25: 716–722 (1998). Because this treatment depurinates DNA every thousand bases or so, this enzyme can not be used to amplify DNA more than a few kilobases in length. Accordingly, the use of this enzyme is most efficient when it is restricted to amplifying target DNA with a length of approximately 200 base pairs.

An additional way of implementing a hot start is to combine the Taq DNA polymerase enzyme with a Taq antibody before adding it to the reagent. This method employs a monoclonal, inactivating antibody raised against Taq DNA polymerase. See Scalice et al., *J. Immun. Methods,* 172: 147–163 (1994); Sharkey et al., *Bio/Technology,* 12:506–509 (1994); Kellogg et al., *Biotechniques,* 16: 1134–1137 (1994). The antibody inhibits the polymerase activity at ambient temperature but is inactivated by heat denaturation. Unfortunately, the antibodies currently available for use in this method are not very efficient, and a 5 to 10-fold molar excess must be used to effect the advantages of a hot start PCR. For Klentaq-278, an amino-terminally deleted *Thermus aquaticus* DNA polymerase that starts with codon 279 which must be used at higher protein levels for long PCR (up to ten times more protein than Taq DNA polymerase), the levels of antibody necessary for a hot start become extremely high and the denatured antibody protein retains some inhibition for longer PCR targets. The original developer of anti-Taq antibodies (Kodak, now Johnson & Johnson) uses a triple-monoclonal antibody mixture which is more effective but is not commercially available and has not been tested in long PCR.

These methods used for hot starts require inclusion of an often expensive component (e.g., anti-Taq antibody) in the reaction mix and may place some undesirable constraints on the performance of the PCR such as a relatively short time period between when a reagent is prepared and when it must be used, or a lower efficiency of amplification.

Yet another method used for hot start PCR is to specially design primers with secondary structures that prevent the primers from annealing until cycling temperatures denature them. See Ailenberg et al., *Biotechniques,* 29: 1018–1020, 1022–1024 (2000). These specially designed primers are usually longer in length and special care must be taken in primer design. It may be inconvenient, expensive, or otherwise infeasible to design such primers.

Besides the grease/wax method, a low tech, inexpensive option of a physical hot start is to add the enzyme, the magnesium and/or the dNTPs to the reactions after they have heated to a temperature sufficient to ensure specificity of primer annealing. This "manual" hot start method, besides being tedious and prone to error, commonly results in contamination and cross-contamination of PCR samples as the reaction tubes must be opened in the thermal cycler while they are hot.

Some PCR users believe they are performing a hot start when they set up PCR reactions in tubes on ice, then add the tubes to a thermal cycler block pre-warmed to 95° C. Although some benefit arises from this method, the addition of only a few nucleotides to a primer can take place every second during the fifteen seconds or more that the tubes warm from 0° to 25° C. This is enough to initiate unwanted competitive PCR for reactions that require a hot start. Also, if many tubes are involved in an experiment, the tubes placed in the block first are heated for a longer time period at 95° C. compared to the tubes placed later in the heating block thus resulting in a lack of reproducibility between samples.

Therefore, the current methods of hot start PCR are associated with multiple shortcomings. In cases of applying physical methods of the hot start, the possible problems include the ease of contamination, plugging up of pipet tips with wax or grease, and increase in time needed to reach target temperatures. In cases of applying chemical/biochemical methods of the hot start, the major drawbacks include the damage to template DNA resulting from harsh conditions needed to activate a chemically inactivated DNA polymerase, the excessive amounts of anti-Amplitaq antibody needed for inactivation of a DNA polymerase prior to initiation of a PCR reaction, and significant costs of obtaining commercially available antibodies. Furthermore, the use of specially designed primers may place unnecessary constraints on PCR reactions.

Accordingly, a need exists for obtaining novel or modified methods of "hot start" PCR that would still provide all advantages of this procedure and at the same time minimize or completely eliminate some of its shortcomings.

SUMMARY OF THE INVENTION

Among the several aspects of the invention, therefore, may be noted the provision of novel processes for performing hot start PCR reactions. Briefly, the present invention is directed to processes for synthesizing nucleic acid extension products and specifically, to methods for amplifying a target nucleic acid sequence using PCR. Accordingly, the present invention provides reagents and kits which can be used to synthesize a nucleic acid extension product.

As such, it is an aspect of the present invention to increase the specificity of PCR product amplification by providing a new method for hot start PCR. In particular, the processes comprise sequestering magnesium ions in a precipitate thereby rendering the DNA polymerase inactive until the magnesium ions are released. In one aspect, the processes of the present invention utilize a reagent which comprises a precipitate containing magnesium. Alternatively, the precipitate is formed by combining a source of magnesium ions and a source of phosphate ions at a temperature of 4° to 30° C. The precipitate is combined with the PCR reaction components e.g., a thermostable DNA polymerase, deoxyribonucleoside triphosphates, a set of primers and a target nucleic acid sequence. The magnesium ions are then released from the precipitate, preferably by heating the mixture to a temperature sufficient to release the magnesium ions from the precipitate and into the mixture. The release of magnesium ions into the mixture activates the DNA polymerase thus allowing the extension of each primer to proceed.

A further aspect of the present invention is to provide kits for amplifying a target nucleic acid. In one embodiment, kits of the present invention comprise a container containing a source of magnesium ions and a container containing a source of phosphate ions which form a precipitate containing magnesium when combined at a temperature of 4° to 30° C., and instructions for amplifying the target nucleic acid. In another embodiment, the kits comprise a container containing a reagent comprising a precipitate containing magnesium and instructions for using the precipitate containing magnesium to amplify the target nucleic acid sequence. Preferably, other reaction reagents such as a DNA polymerase or a mixture of DNA polymerases and deoxyribonucleoside triphosphates are included in the kits of the present invention.

Other aspects and features will be in part apparent and in part pointed out hereinafter.

BRIEF DESCRIPTION OF THE FIGURES

These and other features, aspects, and advantages of the present invention will become better understood with regard to the following description, claims and accompanying drawings where:

In FIG. 4A, lanes 1 and 2 represent the standard molecular weight markers. The PCR reactions from lanes 3–8 were performed in the presence of magnesium chloride, lanes 9–14 were performed in the presence of magnesium sulfate, and lanes 15–20 were done in the presence of magnesium hydroxide. In FIG. 4B, lanes 1 and 2 represent the standard markers and lanes 3–6 were performed in the presence of magnesium carbonate. A manual hot start is represented by lanes 3, 4, 9, 10, 15 and 16 in FIG. 4A and lanes 3 and 4 in FIG. 4B. The regular bench start is shown in lanes 5, 6, 11, 12, 17 and 18 of FIG. 4A and lane 5 in FIG. 4B. The magnesium precipitate hot start is depicted in FIG. 4A in lanes 7, 8, 13, 14, 19, and 20, and lane 6 in FIG. 4B. The superscript represents the milimolar concentrations of the phosphoric acid in the PCR reactions.

In FIG. 5A, lanes 1 and 2 are the molecular weight markers. The PCR reactions in lanes 3–6 were performed using TAT buffer (no phosphate), whereas the PCR reactions depicted in lanes 7–10 were performed using TAT buffer containing 5 mM phosphoric acid. Furthermore, lanes 3, 4, 7, and 8 were performed as manual hot start reactions, whereas lanes 5, 6, 9 and 10 were performed with the magnesium precipitate hot start method. In FIG. 5B, lanes 1 and 2 are the molecular weight markers and lanes 3–6 depict PCR reactions performed using 5 mM $KH_2PO_4$. Lanes 7–10 represent the PCR reactions that were performed using 5 mM $NaH_2PO_4$ and the PCR reactions depicted in lanes 11–14 were performed using 5 mM methylenediphosphonic acid (MDP). In FIG. 5B, lanes 3, 4, 7, 8, 11, and 12 represent manual hot start reactions, and lanes 5, 6, 9, 10, 13, and 14 represent magnesium precipitate hot start PCRs.

FIG. 9 is an image of an agarose gel showing the effect of ammonium sulfate (($NH_4)_2SO_4$) in the TAT buffer on the formation of precipitate and subsequent PCR product (HIV-1 gag) amplification. Lanes 1 and 2 represent the standard molecular weight markers, lanes 3 and 4 represent the manual hot start reactions, and the lanes 5 and 6 represent the bench start. The bench start yielded the wrong band thus indicating the advantage of applying the hot start methods in PCR reactions. Lanes 7–10 represent the magnesium precipitate hot start PCR reactions. The incubation of the phosphoric acid with magnesium chloride was done so that either ammonium sulfate or both Tris and ammonium sulfate were excluded from the buffer. The missing reagents were then added to the reaction tubes with mastermixes prior to running the reactions. Lanes 7 and 8 represent withholding both Tris and ammonium sulfate during the incubation step whereas in the PCR reactions depicted in lanes 9 and 10, only ammonium sulfate was excluded during the incubation.

DETAILED DESCRIPTION

All publications, patents, patent applications or other references cited in this application are herein incorporated by reference in their entirety as if each individual publication, patent, patent application or reference are specifically and individually indicated to be incorporated by reference.

Abbreviations and Definitions

The listed abbreviations and terms, as used herein, are defined as follows:

bp is the abbreviation for base pairs.

kb is the abbreviation for kilobase (1000 base pairs).

nt is the abbreviation for nucleotides.

Taq is the abbreviation for *Thermus aquaticus*.

Pfu is the abbreviation for *Purococcus furiosus*.

Tth is the abbreviation for *Thermus thermophilus*.

"Stoffel fragment" refers to a DNA polymerase having substantially the same amino acid sequence as *Thermus aquaticus* DNA polymerase but lacks the 5' nuclease activity due to a genetic manipulation which results in the deletion of the N-terminal 289 amino acids of the polymerase molecule. See Erlich et al., Science 252:1643, 1991.

"Deep Vent" DNA polymerase is purified from an archael, thermophilic bacterium by New England Biolabs, Inc.

"Klentaq1" is a trademarked commercial name for Klentaq-278 which is a DNA polymerase having substantially the same amino acid sequence as *Thermus aquaticus* DNA polymerase, but excluding the N-terminal 278 amino acids, ±one residue as claimed in U.S. Pat. No. 5,616,494, incorporated herein by reference.

"LA PCR" is Long and Accurate PCR using an unbalanced mixture of two DNA polymerases, as claimed in U.S. Pat. No. 5,436,149.

"KlentaqLA" is an unbalanced mixture of two DNA polymerases, wherein the major component is the thermostable DNA polymerase known as Klentaq1 or Klentaq278 and lacking 3'-exonuclease activity and the minor component is at least one DNA polymerase exhibiting 3'-exonuclease activity, as claimed in U.S. Pat. No. 5,436,149. KlentaqLA is commercially available from Clontech (Cat. No. 8421-1) and from Sigma (Cat. No. D6290). In the examples shown, the minor component is "Deep Vent" DNA polymerase.

"TaqLA" is an unbalanced mixture of two DNA polymerases, wherein the major component is full-length Taq DNA polymerase as the thermostable DNA polymerase lacking 3'-exonuclease activity and the minor component is at least one DNA polymerase exhibiting 3'-exonuclease activity, as claimed in U.S. Pat. No. 5,436,149, incorporated herein by reference. In the examples shown, the minor component is "Deep Vent" DNA polymerase.

"Thermostable" is defined herein as having the ability to withstand temperatures up to at least 95° C. for many minutes without becoming irreversibly denatured and the ability to polymerize DNA at optimum temperatures of 55° C. to 75° C.

In vitro processes of producing replicate copies of the same polynucleotide, such as PCR, are collectively referred to herein as "amplification" or "replication." For example, single or double stranded DNA may be replicated to form another DNA with the same sequence. RNA may be replicated, for example, by a RNA directed RNA polymerase, or by reverse transcribing the RNA using a reverse transcriptase or a DNA polymerase exhibiting reverse transcriptase activity and then performing a PCR amplification. In the latter case, the amplified copy of the RNA is a DNA (known as "complementary DNA" or "cDNA") with the correlating or homologous sequence.

The polymerase chain reaction ("PCR") is a reaction in which replicate copies are made of a target polynucleotide using one or more primers, and a catalyst of polymerization, such as a DNA polymerase, and particularly a thermally stable polymerase enzyme. Generally, PCR involves repeatedly performing a "cycle" of three steps: "melting", in which the temperature is adjusted such that the DNA dissociates to single strands, "annealing", in which the temperature is adjusted such that oligonucleotide primers are permitted to match their complementary base sequence using base pair recognition to form a duplex at one end of the span of polynucleotide to be amplified; and "extension" or "synthesis", which may occur at the same temperature as annealing, or in which the temperature is adjusted to a slightly higher and more optimum temperature, such that oligonucleotides that have formed a duplex are elongated with a DNA polymerase. This cycle is then repeated until the desired amount of amplified polynucleotide is obtained. Methods for PCR amplification are taught in U.S. Pat. Nos. 4,683,195 and 4,683,202.

"Specificity" in PCR amplification refers to the generation of a single, "specific," PCR product with the size and sequence predicted from the sequences of the primers and the genomic or transcribed region of nucleic acid to which the primers were designed to anneal in a base-complementary manner. "Nonspecific" PCR product has a size or sequence different from such prediction. A "target nucleic acid" is that genomic or transcribed region of nucleic acid, the ends of which are base-complementary (with proper orientation) to primers included in a complete set of PCR reagents. A primer refers to a nucleic acid sequence, which is complementary to a known portion of a target nucleic acid sequence and which is necessary to initiate synthesis by DNA polymerase. "Proper orientation" is for the two primers to anneal to opposite strands of double-stranded target nucleic acid with their 3' ends pointing toward one another. Such primers are said to target the genomic or transcribed sequence to the ends of which they are base-complementary. An "appropriate temperature", as referred to in the claims in regard to the PCR amplifications, indicates the temperature at which specific annealing between primers and a target nucleic acid sequence occurs.

"Manual hot start PCR" is a PCR method that generally produces improved reliability, improved products from low-copy targets, and/or cleaner PCR products. Template DNA and primers are mixed together and held at a temperature above the threshold of non-specific binding of primer to template. All of the PCR reaction components are added to the extension reaction except one critical reagent which is withheld. The withheld reagent is usually the thermostable polymerase or the magnesium, but it can also be, for instance, the triphosphates or the primers. Just prior to the cycling, the withheld reagent is added to allow the reaction to take place at higher temperature. Due to lack of non-specific hybridization of primers to template or to each other, the PCR amplification proceeds more efficiently as a result of the reduction or elimination of competing extensions at non-target locations.

"Standard or bench start" are used interchangeably herein and when used to refer to PCR amplification, indicate that all the PCR reaction components needed for amplification are added to the template nucleic acid sequence at 25° C.

"Warm start" is used herein and when used to refer to PCR amplification, indicates that all the PCR reaction components needed for amplification are added to the template nucleic acid sequence at 25° C. followed by an incubation at 30° for 30 minutes.

When referring to a particular DNA polymerase, the term "polymerase activity" refers to the ability of the DNA polymerase to incorporate dNTPs or ddNTPS in a chain extension reaction.

"Reverse transcription" or "reverse transcribing" refers to the process by which RNA is converted into cDNA through the action of a nucleic acid polymerase such as reverse transcriptase. Methods for reverse transcription are well known in the art and described for example in Fredrick M. Ausubel et al. (1995), "Short Protocols in Molecular Biology," John Wiley and Sons, and Michael A. Innis et al. (1990), "PCR Protocols," Academic Press.

"*Thermus aquaticus* DNA polymerase" or "Taq DNA polymerase" are used interchangeably to refer to heat stable DNA polymerases from the bacterium *Thermus aquaticus* and include all Taq mutants, natural and synthesized.

The procedures disclosed herein which involve the molecular manipulation of nucleic acids are known to those skilled in the art. See generally Fredrick M. Ausubel et al. (1995), "Short Protocols in Molecular Biology," John Wiley and Sons, and Joseph Sambrook et al. (1989), "Molecular Cloning, A Laboratory Manual," second ed., Cold Spring Harbor Laboratory Press, which are both incorporated by reference.

Accordingly, the present invention provides processes and kits for performing a "hot start" PCR. The processes and kits utilize the step of sequestering magnesium ions in a precipitate prior to the extension step of the PCR reaction thereby rendering a DNA polymerase inactive until the mixture the magnesium ions are released from the precipitate. As a result, amplification of target DNA molecules is specific with minimal or no formation of competitive or inhibitory products. Thus, the processes and kits for amplification of a nucleic acid have improved efficacy which is achieved by preventing a significant catalytic reaction of DNA polymerase with other reagents until the extension cycle of PCR.

The hot start PCR of the present invention is achieved by forming a precipitate comprising magnesium ions which sequesters the magnesium ions from other PCR reagents and preferably, prevents significant DNA polymerase activity due to the lack of magnesium ions in the reaction mixture. As such, the magnesium ions required for DNA polymerase activity are withheld from the DNA polymerase and other PCR reagents prior to the transfer of the tubes into the thermal cycler. The precipitate is formed by combining a source of magnesium ions and a source of phosphate ions for at least 3 minutes at a temperature ranging from 4° to 30° C. The magnesium ions utilized in the present invention are available from different sources. Preferably, the sources of magnesium ions include but are not limited to magnesium chloride, magnesium hydroxide, magnesium carbonate and magnesium sulfate. In a preferred embodiment, the source of magnesium ions is magnesium chloride, which is most commonly used in PCR reactions. The concentration of magnesium needed for the magnesium precipitate hot start is similar to the concentration that is needed for a manual hot start. Preferably, the concentration of magnesium chloride in the present invention is about 3.5 mM.

Many sources of phosphate ions are available in the art. Preferably, the sources of phosphate ions include but are not limited to phosphoric acid ($H_3PO_4$), potassium phosphate ($K_2HPO_4$), and ammonium phosphate (($NH_4$)$_2HPO_4$). In a preferred embodiment, the source of phosphate ions is ammonium phosphate or phosphoric acid and more preferably, the source of phosphate ions utilized is phosphoric acid. The concentrations of the phosphoric acid that are suitable for magnesium precipitate hot start range from about 3 mM to 13 mM and preferably, the concentration of phosphoric acid is between 5 mM and 7 mM. Alternatively, if ammonium phosphate is the source of the phosphate ions, the concentration of ammonium phosphate ranges from 2 mM to 6 mM.

Preferably, the source of phosphate ions is contained in a solution which is buffered to a pH above 7. In a preferred embodiment, the buffer contains Tris (Tris(hydroxymethyl) aminomethane) and more preferably, ammonium sulfate to aid in the production of the precipitate during the magnesium precipitate hot start method. Preferably, the buffer used in the present invention is TAT buffer (50 mM Tris-HCl with pH 9.2, 16 mM ammonium sulfate, and 0.1% Tween 20) having a final pH of approximately 9.1. In a preferred embodiment, the source of the phosphate ions is premixed with the TAT buffer prior to the formation of the precipitate. Accordingly, when TAT buffer containing a source of phosphate ions, ammonium sulfate, and Tris is incubated with a source of magnesium ions, ammonium sulfate and Tris contribute to formation of the precipitate. Preferably, the TAT buffer used in the processes employs phosphoric acid as the source of phosphate ions. As shown in the Example 8, ammonium sulfate and Tris are not essential for the formation of the precipitate and execution of the magnesium precipitate hot start; however, the use of ammonium sulfate and Tris in the buffer enhances the precipitation reaction and the amplification of the products.

The incubation of phosphoric acid with magnesium ions in the presence of TAT buffer for approximately 3 minutes at a low temperature, preferably below 34° C., produces an insoluble precipitate comprising magnesium and phosphate. In yet another preferred embodiment, the source of magnesium ions and the source of phosphate ions are incubated at a temperature of 0° to 30° C. Preferably, the source of magnesium ions and the source of phosphate ions are incubated at a temperature of at least 4° C. In another preferred embodiment, the source of magnesium ions and the source of phosphate ions are incubated at a temperature of at least 25° C. The source of magnesium and the source of phosphate are incubated for at least three minutes to form the precipitate containing magnesium. Preferably, the source of magnesium and the source of phosphate are incubated for at least 5 minutes and more preferably, for at least 10 minutes.

Once the precipitate is formed, the additional PCR reaction components are added. Such PCR reagents include at least one DNA polymerase, deoxyribonucleoside triphosphates, at least one primer and at least one target nucleic acid sequence. Preferably, the DNA polymerases are thermally stable DNA polymerases. Some examples of thermally stable DNA polymerases include, but are not limited to, *Thermus aquaticus* DNA polymerase, N-terminal deletions of Taq DNA polymerase such as Stoffel fragment DNA polymerase, Klentaq235, and Klentaq-278 ; *Thermus thermophilus* DNA polymerase; *Bacillus caldotenax* DNA polymerase; *Thermus flavus* DNA polymerase; *Bacillus stearothermophilus* DNA polymerase; and archaebacterial DNA polymerases such as *Thermococcus litoralis* DNA polymerase (also referred to as Vent), Pfu, Pfx, Pwo, and Deep Vent or a mixture of DNA polymerases. In a preferred embodiment, the DNA polymerases are TaqLA, KlentaqLA, Klentaq1, Pfu, Deep Vent or Tth. More preferably, the DNA polymerases are TaqLA, Klentaq1, and KlentaqLA.

After the precipitate is combined with other PCR reagents, the magnesium ions are released from the precipitate thereby activating the DNA polymerase. Preferably, the magnesium ions are released from the precipitate by heating the reaction mixture to a temperature above 30° C. However, other methods may be used to release the magnesium ions from the precipitate and into the reaction mixture e.g., chemical reactions, pH changes. The ability to quickly release magnesium ions from the precipitate results in the amplification of the specific target nucleic acid sequence with minimal or no formation of competitive or inhibitory products. As DNA polymerases require magnesium in order to synthesize nucleic acid extension products, the release of the magnesium ions into the mixture results in the extension of the target nucleic acid molecules. Preferably, the mixture containing the precipitate and PCR reaction reagents is heated to standard cycling temperatures (50°–95° C., preferably 68° C.) so that the magnesium is released from the precipitate at a higher temperature than the temperature at which mispriming occurs. In this way, the magnesium precipitate hot start method provides a significantly improved specificity of PCR target amplification compared to the standard PCR reactions. The temperature at which the magnesium ions are released is achieved during the first cycle of the PCR amplification in the thermal cycler thereby eliminating any extra steps and need for additional reagents.

In addition to the applicability of this invention in standard PCR reactions, the formation of a precipitate containing magnesium could be utilized in "long and accurate" PCR. Specifically, "long and accurate" PCR could conveniently be provided the advantages of a hot start without tedious extra care or steps thus resulting in increased reliability and efficiency of human STR typing and multiplex PCR. Such long and accurate PCR is described in Barnes, *Proc. Natl. Acad. Sci. USA*, 91:2216–2220 (1994) and in U.S. Pat. No. 5,436,149. Furthermore, the magnesium precipitate hot start method can be applied in the RT-PCR reaction, wherein the desired RNA sequence is first reverse transcribed into the cDNA, and then amplified by PCR. Besides a greater specificity of product amplification, the magnesium precipitate hot start method possesses other beneficial attributes such as the ease of manipulation, the little extra time necessary to perform it, and the inexpensive reagents required.

Further, the present invention may be utilized in any process which requires amplification. For instance, the formation of a precipitate containing magnesium may be utilized in processes of in vivo footprinting which use a DNA polymerase to amplify the DNA. In general, analysis of the interaction of proteins with either DNA or RNA by in vivo footprinting involves first modifying the nucleic acids by the footprinting reagent in situ. Footprinting reagents are chosen based on how extensively the reactivity of a nucleic acid toward the modifying agent is altered upon interaction with the binding protein of interest. The modifications are then visualized (i.e., the analysis of the reactivity of each nucleotide of the sequence of interest) usually by PCR. See Grange et al., *Methods*, (1997) 11:151–63. Accordingly, LM-PCR is utilized to visualize modifications in DNA molecules and RL-PCR is utilized to visualize modifications in RNA molecules. Both LM-PCR and RL-PCR involve ligating a linker to the unknown 5'-ends resulting from the in vivo footprinting analysis and exponentially amplifying the region of interest. In LM-PCR, a blunt double-stranded end is created using a gene specific primer and a DNA polymerase. Then a partially double—stranded DNA linker with one blunt end is ligated to the blunt ends using a DNA ligase. The strand onto which the linker has been ligated will then serve as a template for PCR amplification. Similarly, in RL-PCR, a single stranded RNA linker is ligated to the 5' P-ends of all RNA molecules using a RNA ligase. Then a cDNA copy of the sequence of interest is synthesized using a reverse transcriptase which results in generating templates for PCR amplification. Lastly, amplified products from LM-PCR and RL-PCR are then labeled and sequenced for analysis.

A precipitate containing magnesium is also applicable to processes of primer directed mutagenesis using DNA polymerases to amplify the mutated nucleic acid sequences having substitution mutations within the target DNA sequence. The process of primer directed mutagenesis comprises contacting a nucleic acid sequence with two mutated primers, where each mutation is a mismatch when compared to the template sequence; amplifying using DNA polymerase; and allowing the amplified products to reanneal. The resulting nucleic acid molecules amplified using these mismatched mutated primers have mismatched bases and have a double-stranded region containing a mutant strand. See Innis et al., "PCR Protocols", Academic Press, 1990, pp. 177–183.

The use of a precipitate containing magnesium is further applicable to processes of DNA restriction digest filling using DNA polymerases to amplify the DNA. DNA polymerases are used in restriction digest filling to extend the 3' ends resulting from digestion with restriction enzymes for the purpose of producing 5'-sticky ends. The process comprises separating the digested DNA strands; contacting each 3' end of the separated nucleic acid molecules with oligodeoxyribonuclotide primers; extending the 3' ends using DNA polymerase to create blunt ends; and allowing the DNA strands with the newly synthesized 3' ends to reanneal to its complementary strand.

In a further aspect, the present application provides kits for the use of the magnesium precipitate hot start in PCR reactions. Accordingly, a reagent containing a pre-formed precipitate containing a source of phosphate ions and a source of magnesium ions and other PCR reagents are provided in the form of a test kit, that is, in a packaged collection or combination as appropriate for the needs of the user. Instructions for utilizing a precipitate containing magnesium in a process of amplifying a target nucleic acid are provided in the kits of the present invention. Preferably, the kit provides a pre-formed precipitate containing magnesium ions and instructions for utilizing the precipitate to amplify a nucleic acid sequence. In another embodiment, the kit comprises a container comprising a source of phosphate ions and a container comprising a source of magnesium ions, wherein combining two sources at a temperature of below 34° C. results in the formation of a precipitate, and instructions for using the source of phosphate ions and a source of magnesium ions to amplify a target nucleic acid. The kit can of course include appropriate packaging, containers, labeling, and buffers for amplifying a target nucleic acid. In another preferred embodiment, the kit also includes a DNA polymerase and more preferably, deoxyribonucleoside triphosphates. In another embodiment, a kit comprises instructions for using a source of phosphate ions and a source of magnesium ions in amplifying a target nucleic acid sequence.

The following examples illustrate the invention.

EXAMPLES

Example 1
The Effect of Phosphoric Acid Concentration on PCR Product Amplification The human tissue plasminogen activator (t-PA) gene was amplified using different hot start PCR methods. The standard PCR program for this gene included holding the reaction for 3 minutes at 68° C., after which 40 cycles were performed with the following parameters: 93° C. for 50 seconds, 67° C. for 40 seconds, and 68° C. for 5 minutes. The primers for the amplification of human t-PA gene were:

t-PA forward 7: GGAAGTACAGCTCAGAGTTCTG-CAGCACCCCTGC (SEQ. ID. NO. 1)

t-PA reverse 7.5: TGGGATTATAGACACGAGCCACT-GCACCTGGCCC (SEQ. ID. NO. 2).

The choice of primers follows Degen et al., *J. Biol. Chem.*, 261(15):6972–6985 (1986) and Flynn S. (unpublished, 2000). The enzyme that was used was KlentaqLA. The expected size of the product was 880 bp. In addition to the standard protocol, all the samples in FIG. 1 were incubated at 30° C. for 30 minutes prior to the first step of the PCR reaction (warm start). This step was included as a control for the efficacy of the magnesium precipitate hot start.

The manual hot start was achieved by adding 5 ul of 35 mM magnesium chloride after 30 seconds at 68° C. (hot start is denoted in FIGS. 1 and 2 with a letter H), whereas magnesium chloride was added at room temperature to warm start reactions. The warm start involving the additional step of incubation at 30° C. for 30 minutes was denoted with a letter W in FIG. 1. B denotes a standard or bench PCR protocol, wherein all PCR reagents are mixed and are directly transferred to the cycler. The superscript designation in FIGS. 1 and 2 denotes the concentration of phosphoric acid in the reaction, which was included in the TAT buffer. For the magnesium precipitate hot start, the appropriate TAT buffer (4.5 ul) was incubated with 35 mM magnesium chloride (5 ul)for at least 10 minutes at room temperature to allow precipitate to form, after which the master mix was added to the tubes. The mastermix contained the following:

10 mM each dNTP (each 0.5 ul/rxn)

10 ul tPA forward primer (1 ul/rxn)

10 ul tPA reverse primer (1 ul/rxn)

10 ng/ul human DNA (0.05 ul/rxn)

5 M Betaine (13 ul/rxn)

100% DMSO (0.75 ul/rxn), and

KlentaqLA Mix (5 ul/rxn), wherein KlentaqLA Mix consisted of 2.25 ul KlentaqLA, 15 ul TAT, and 132.75 ul $dH_2O$, and sufficient volume of $dH_2O$ so that the total volume of the reaction is 50 ul.

The reactions were then run in the RoboCycler40 thermocycler at the previously specified conditions. The amplification products were observed on the agarose gel stained with ethidium bromide.

Figure 1:
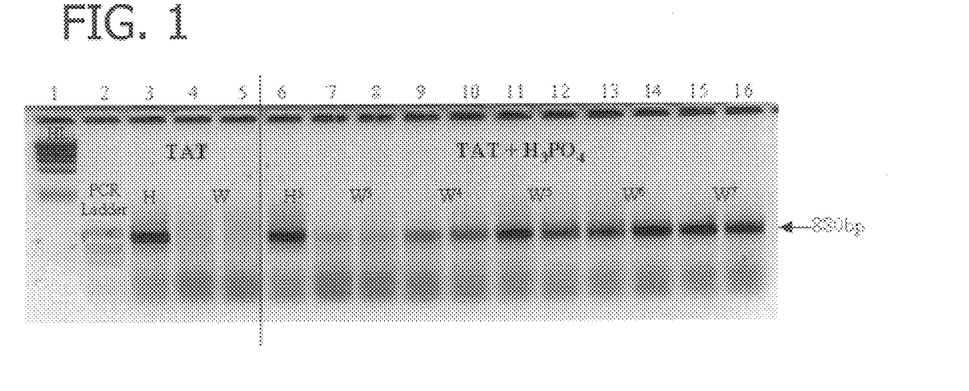
FIG. 1 is an image of an agarose gel depicting the amplification products of hot start PCR reactions performed using different concentrations of phosphoric acid (3–7 mM) added to magnesium chloride in TAT buffer. Lanes 1 and 2 represent the standard molecular weight ladders. The PCR reactions in lanes 3 and 6 were performed by a manual hot start method and the PCR reactions in the remaining lanes were prepared at room temperature and incubated at 30° C. for 30 minutes (warm start). The PCR products represented in lanes 3–5 were formed without any phosphoric acid in the TAT buffer whereas the products in other lanes (6–16) were formed utilizing TAT buffer containing phosphoric acid ranging in concentration from 3 mM to 7 mM (TAT3–TAT7). In lanes 7–16, this buffer was initially incubated with magnesium chloride to form the precipitate. The superscript represents the milimolar concentrations of phosphoric acid in the PCR reactions.
Figure 2:
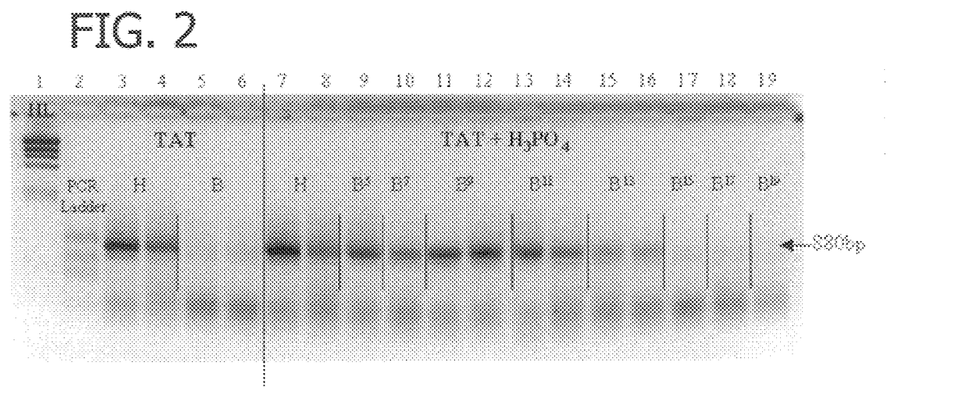
FIG. 2 is an image of an agarose gel depicting the amplification products of hot start PCR reactions performed using different concentrations of phosphoric acid (5–19 mM) added to magnesium chloride in TAT buffer. Lanes 1 and 2 represent the standard molecular weight markers. Lanes 3, 4, 7, and 8 are representations of a manual hot start, whereas the standard/bench start is portrayed in lanes 5 and 6. The remaining lanes contain the products from PCR reactions that were performed by using the magnesium precipitate hot start method. Specifically, lanes 9–19 depict PCR products that were formed as a result of PCR reactions utilizing TAT buffers containing different phosphoric acid concentrations. The superscript represents the milimolar concentrations of phosphoric acid in each PCR reaction.

In FIG. 1, the concentration of phosphoric acid ranged from 3 mM to 7 mM, whereas in FIG. 2 it ranged from 5 mM to 19 mM. As can be seen from the Figures, the magnesium precipitate hot start was as efficient as the manual hot start. The optimal concentration range of phosphoric acid in the manual hot start is between 5 mM and 7 mM, however the method still works well at concentrations between 3 mM and 13 mM.

The procedure as specified above was also performed with incubations taking place at 34° C. and 37° C.; however, the magnesium precipitate PCR reactions did not work as effectively as manual hot start reactions at these temperatures (data not shown).

Figure 3:
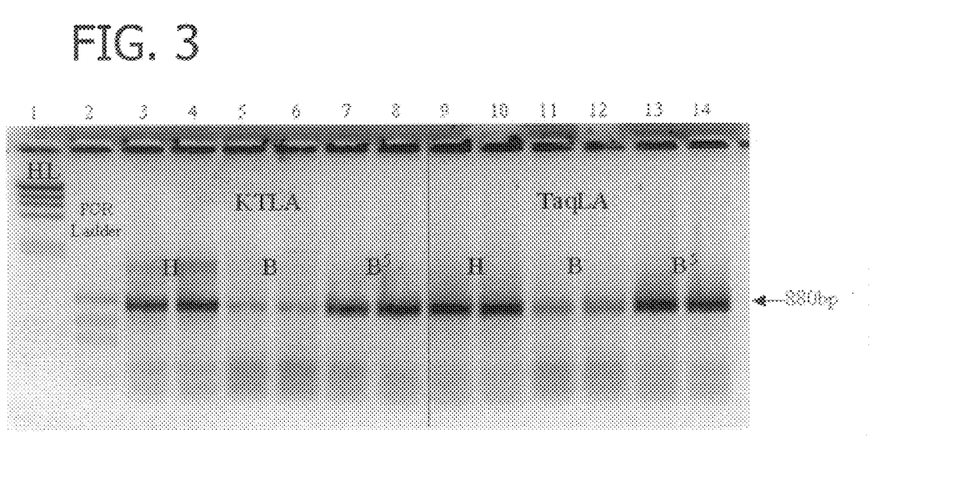
FIG. 3 is an image of an agarose gel of a magnesium precipitate hot start PCR using TaqLA and KlentaqLA. Lanes 1 and 2 represent the standard molecular weight markers. Lanes 3 and 4 and lanes 9 and 10 represent the products of the manual hot start method performed with KlentaqLA and TaqLA, respectively. Lanes 5 and 6 and lanes 11 and 12 show minimal amplification of the products when using regular PCR methods (bench start) using KlentaqLA and TaqLA, respectively. Lanes 7 and 8 and lanes 13 and 14 illustrate the use of KlentaqLA and TaqLA in magnesium precipitate hot start reactions. The superscript represents the milimolar concentrations of phosphoric acid in the PCR reactions.

Example 2
The Use of Different Polymerases in the Magnesium Phosphate Hot Start Method The human t-PA gene was amplified using the standard PCR protocol described in Example 1. In addition, TaqLA Mix that was also used in this Example 2 consisted of 5 ul TaqLA, 5 ul TAT, and 40 ul $dH_2O$. The reactions were run in duplicate, and each of the hot start (H), bench start (B) or bench start with phosphoric acid (i.e. $B^5$ or the magnesium precipitate hot start method) was performed with both KlentaqLA and TaqLA (for either enzyme, 5 ul of the enzyme mix was used per reaction). The bands in FIG. 3 depict the products of these reactions. The bench start yielded very light bands, indicating that the specificity of the reaction was suboptimal whereas both the manual and the magnesium precipitate hot start reactions resulted in high amplification of the product with both KlentaqLA and TaqLA. The data suggest that multiple DNA polymerases can be utilized to perform magnesium precipitate hot start PCR with similar efficiencies.

Example 3
The Effect of Varying Phosphate Comprising Compounds on PCR Product Amplification Human t-PA gene was amplified with KlentaqLA using the standard protocol from Example 1 either utilizing the manual hot start method (magnesium chloride added at 68° C. after 30 seconds) or the magnesium precipitate hot start method. For the magnesium precipitate hot start, TAT buffers containing different phosphate comprising compounds were formulated. The following compounds were used: phosphoric acid ($H_3PO_4$), potassium phosphate ($KH_2PO_4$), sodium phosphate ($NaH_2PO_4$), and MDP (methylenediphosphonic acid, ($CH_6O_6P_2$), each at a final concentration of 5 mM in the reaction. The resulting pHs were:

8.8–TAT+5 mM phosphoric acid
9.1–TAT+5 mM $KH_2PO_4$
9.2–TAT+5 mM $NaH_2PO_4$
8.7–TAT+5 mM MDP.

Figure 5A:
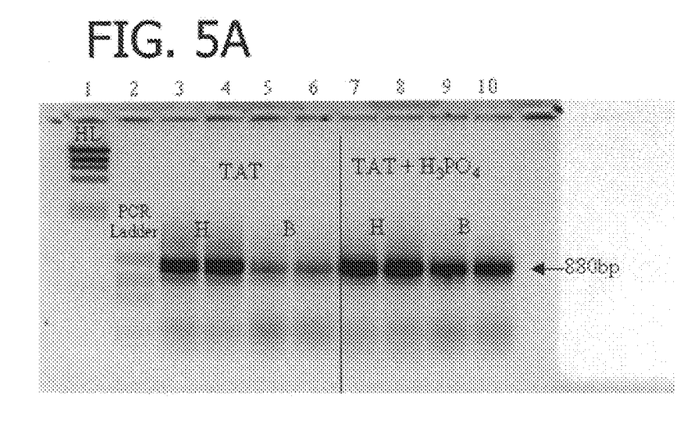
FIGS. 5A and 5B are images of agarose gels depicting the magnesium precipitate hot start method utilizing different phosphate containing compounds, including $H_3PO_4$, $KH_2PO_4$, $NaH_2PO_4$, and $CH_6O_6P_2$.
Figure 5B:
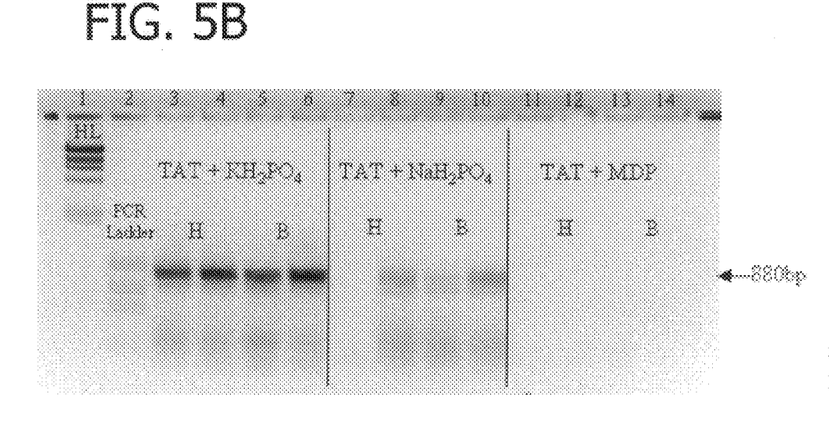

As FIG. 5 shows, the reactions performed with TAT buffer generated well amplified products only with the manual hot start whereas bench start resulted in low amplification. The reactions containing phosphoric acid and $KH_2PO_4$ yielded bands on the gel, however the phosphoric acid was superior in performance compared to $KH_2PO_4$. The reactions with $NaH_2PO_4$ generated hardly any amplifications products, and there were no products in the reactions with MDP indicating that these two compounds are not the adequate choices for performing hot start PCR reactions. However, some optimization of $KH_2PO_4$ might render it suitable for use in magnesium precipitate hot start PCR. At present, the phosphoric acid is the most adequate source of phosphate ions for the magnesium precipitate hot start.

Figure 6:
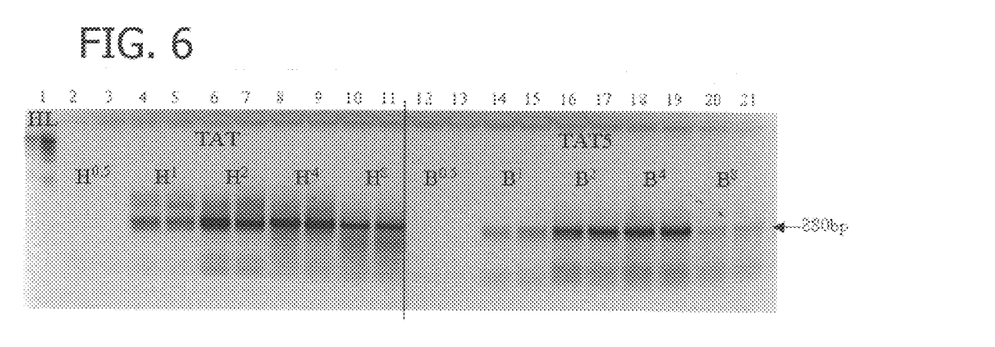
FIG. 6 is an image of an agarose gel depicting the effect of magnesium chloride concentration on precipitate formation and the efficacy of the magnesium precipitate hot start PCR. Lane 1 is a standard molecular weight marker, lanes 2–11 were performed as manual hot start PCRs in the presence of the TAT buffer and increasing concentrations of magnesium chloride and lanes 12–21 were performed as magnesium precipitate hot start reactions in the presence of TAT5 buffer and increasing magnesium chloride concentrations. The superscript represents the final milimolar concentrations of the magnesium chloride used in the PCR reactions.

Example 4
The Effect of Magnesium Chloride Concentration on Precipitate Formation The human t-PA gene was amplified using the standard protocol described in Example 1. FIG. 6 shows the effect of varying magnesium chloride concentration in manual and hot start PCRs. The DNA polymerase used in both methods was TaqLA. The manual hot start reactions were performed with TAT buffer while the magnesium precipitate hot start PCR reactions were performed with TAT5. The concentrations of magnesium chloride that were tested included 0.5 mM, 1 mM, 2 mM, 4 mM, and 8 mM. The magnesium chloride concentration of 0.5 mM resulted in no amplification of the product in either manual or magnesium precipitate hot start and at concentrations of 2 mM and 4 mM both PCR methods worked well. At the high concentration of magnesium (8 mM) the manual hot start worked better than the magnesium precipitate method. This was expected, since at high concentrations of magnesium, there was not enough phosphate in the solution to sequester a significant proportion of magnesium ions, thereby allowing DNA polymerase to extend the primers. However, the concentration curve of magnesium indicated that the magnesium precipitate hot start is effective over the range of magnesium concentrations commonly used in PCR.

Example 5
The Time of Incubation Influences the Precipitate Formation

Figure 7:
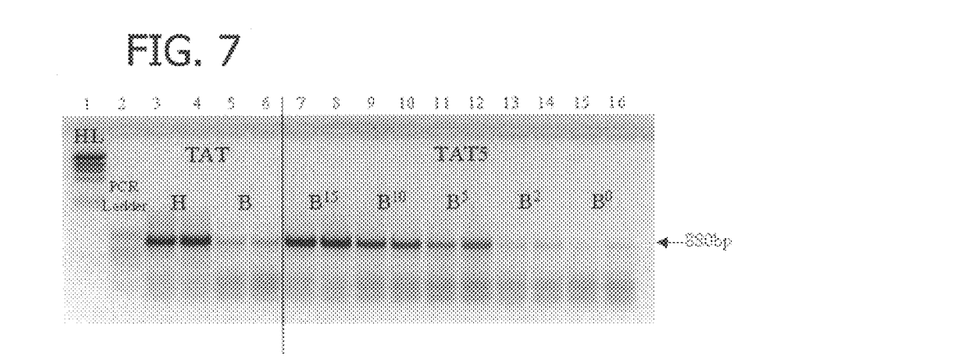
FIG. 7 is an image of an agarose gel depicting the effect of incubating TAT5 buffer with magnesium chloride for various lengths of time. Lanes 1 and 2 represent molecular weight markers, lanes 3 and 4 depict the manual hot start method and lanes 5 and 6 represent the regular bench start. Lanes 7–16 depict the products of the magnesium precipitate hot start PCR reactions. TAT5 and magnesium chloride were allowed to incubate during the magnesium precipitate hot start reactions for 15 minutes (lanes 7 and 8), 10 minutes (lanes 9 and 10), 5 minutes (lanes 11 and 12), 2 minutes (lanes 13 and 14), and 0 minutes (lanes 15 and 16). The superscripts represent minutes of incubation of TAT5 and magnesium chloride.

Human t-PA gene was amplified using the standard protocol described in Example 1. The manual hot start (H) and the bench start (B) were performed with TAT buffer. The hot start resulted in a significant amplification of the t-PA gene, whereas the bench start yielded a minimal band. For the magnesium precipitate hot start reactions, TAT5 buffer was incubated with magnesium chloride for different lengths of time prior to the addition of the mastermix. All the reactions mentioned in this example and depicted in FIG. 7 were performed with KlentaqLA. The reactions were done in duplicate, and the incubation times were 15 minutes, 10 minutes, 5 minutes, 2 minutes, and 0 minutes. It can be seen from the figure that no incubation time or 2 minutes are not long enough for the precipitate to form and simulate a hot start. At 5 minutes, there is a slight amplification of the product, however the best amplification is observed after 15 minutes of incubation. This data suggests that in order for the magnesium precipitate hot start to function properly a source of phosphate and a source of magnesium need to be incubated for at least 5 minutes, with the amplification significantly improving after 10–15 minutes of incubation.

Example 6
The Universality of the Magnesium Precipitate Hot Start Method Examples 1–5 have shown that the magnesium precipitate hot start method works efficiently with the human t-PA gene. In order to show that this method is not limited to certain genes, the same method was utilized to amplify a viral gene. The gene utilized was HIV-1 gag. The primers for the amplification of HIV-1 gag were:

SK 38: ATAATCCACCTATCCCAGTAGGAGAAAT (SEQ. ID. NO. 3)
SK39: TTTGGTCCTTGTCTTATGTCCAGAATGC (SEQ. ID. NO. 4).

These primers and the HIV-1 DNA were supplied by Applied Biosystem's GeneAmplimer HIV-1 Control Reagents. The use of the primers is disclosed in Ou et al., *Science* 239: 295–297 (1998).

The PCR program for amplification of this gene included holding the reaction at 68° C. for 3 minutes followed by 42 cycles with the following conditions: 95° C. for 40 seconds, 52° C. for 40 seconds, and 68° C. for 1 minute. The mastermix contained:

10 mM each DNTP (each 0.5 ul/rxn)
25 um SK 38 primer (0.5 ul/rxn)
25 uM SK 39 primer (0.5 ul/rxn)
25 copies/ul HIV-1 DNA+100 ng/ul denatured human DNA (1 ul/rxn)

Klentaq1 Mix (5 ul/rxn), wherein said mix consisted of 2 ul Klentaq1, 20 ul TAT, and 178 ul dH$_2$O, and sufficient dH$_2$O for the total reaction volume of 50 ul.

For the magnesium precipitate hot start, 5 ul of 35 mM magnesium chloride was added to a reaction tube containing 4.5 ul TAT5 and incubated for at least 10 minutes at room temperature to allow the precipitate to form. The mastermix was then prepared and added to the tubes for both manual and magnesium precipitate hot starts (magnesium was excluded for the manual hot start, and then added to the appropriate tubes in the cycler after 30 seconds at 68° C.).

Figure 8:
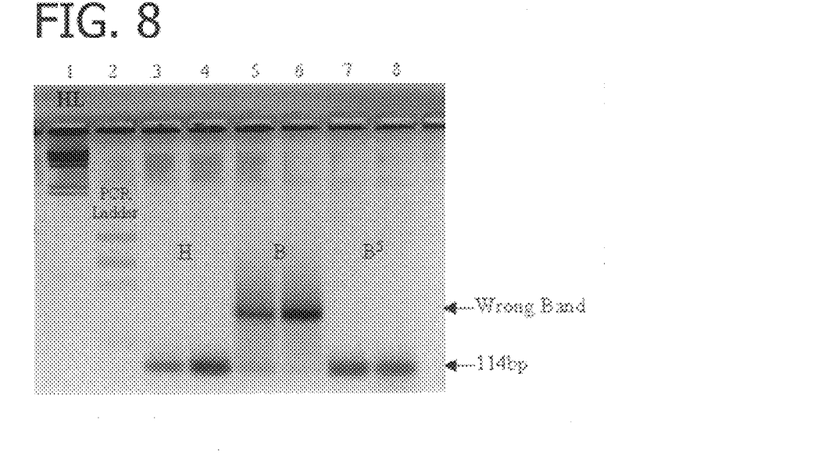
FIG. 8 is an image of an agarose gel depicting use of the magnesium precipitate hot start method to amplify HIV-1 gag gene. Lanes 1 and 2 depict the molecular markers, lanes 3 and 4 depict the manual hot start, lanes 5 and 6 depict the bench start method, and lanes 7 and 8 depict the magnesium precipitate hot start reaction. The bench start method of performing PCR resulted in the amplification of an incorrect band thus showing the lack of specificity. However, both the manual and magnesium precipitate hot starts yielded the bands of correct size. The superscript represents the milimolar concentration of phosphoric acid utilized in the reaction.

The results of the FIG. 8 show that the bench start was very non-specific, generating an incorrect band whereas the magnesium precipitate hot start, similar to the manual hot start was very specific and resulted in a significant amplification of the gag gene.

Figure 4A:
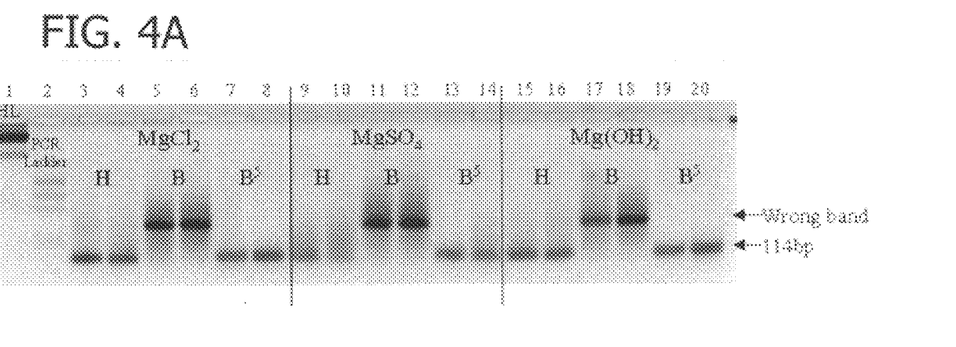
FIGS. 4A and 4B are images of agarose gels depicting the magnesium precipitate hot start method utilizing different magnesium comprising compounds including magnesium chloride ($MgCl_2$), magnesium sulfate ($MgSO_4$), magnesium hydroxide ($Mg(OH)_2$) and magnesium carbonate ($MgCO_3$).
Figure 4B:
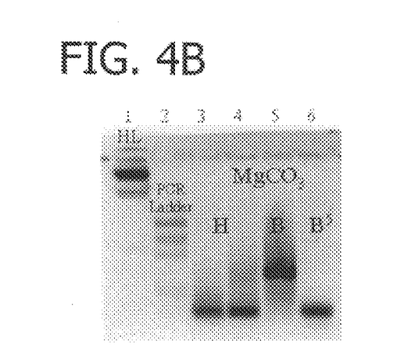

Example 7
Various Magnesium Containing Compounds can Result in Precipitate Formation Different magnesium containing compounds were tested for the ability to form a precipitate with phosphoric acid and to facilitate the magnesium precipitate hot start method. The compounds tested were magnesium chloride, magnesium sulfate, magnesium hydroxide, and magnesium carbonate. As shown in Examples 1–6, magnesium chloride was previously tested and shown to work in the magnesium hot start methods. Thus, magnesium chloride was utilized in this Example 7 as a positive control. The PCR program and the protocols for performing bench start, manual start and magnesium precipitate hot starts are described in the previous examples. As seen in FIGS. 4a and 4b, the bench start reactions performed with all four magnesium containing compounds yielded the bands of incorrect size. The manual hot start reactions worked well with magnesium chloride, magnesium hydroxide, and magnesium carbonate, whereas the manual hot start performed with magnesium sulfate generated very little product. The magnesium precipitate hot start method worked efficiently with all four magnesium containing compounds (magnesium chloride, magnesium sulfate, magnesium hydroxide, and magnesium carbonate). This could prove to be useful in PCR reactions wherein the DNA polymerases require magnesium in a form other than the most commonly used magnesium chloride.

Example 8
The Effect of Ammonium on Precipitate Formation

Figure 9:
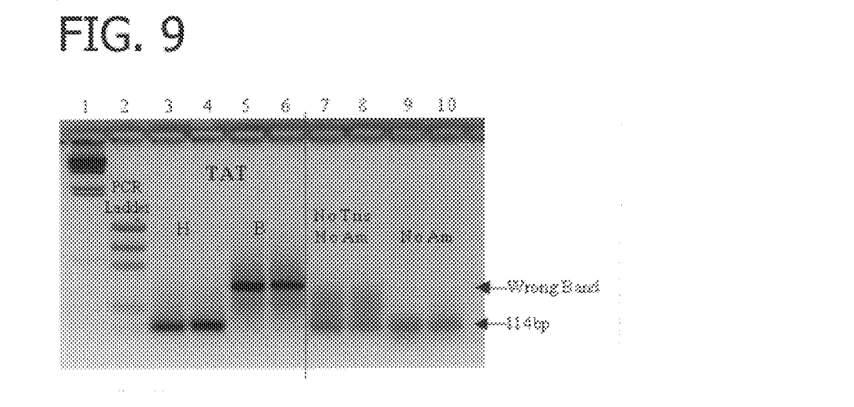

The gene that was amplified in this Example 8 was HIV-1 gag and its amplification was performed according to the protocol specified in Example 6. The changes from that protocol include the use of 50 copies of HIV genome instead of 25 copies and the cycling in the RoboCycler was performed 44 times rather than 42 times. The reactions that were prepared and run in the cycler were the manual hot start, the bench start, and reactions that omitted either ammonium sulfate or both Tris and ammonium sulfate during the incubation step. In the reaction where both ammonium sulfate and Tris were withheld, the mixture of 100 ul 35 mM magnesium chloride and 100 ul of 50 mM phosphoric acid was incubated for 24 hours at room temperature and then for additional 12 hours at 4° C. For the reaction where only ammonium sulfate was withheld, 50 ul of 1 M Tris Base was added to the mixture of the same composition as above and incubated at the same conditions. Prior to the transfer into the thermal cycler, 10 ul of the first mixture and 12.5 ul of the second mixture were added to the tubes. The appropriate missing reagents were then added to both tubes and the reactions were subjected to the amplification in the cycler. It can be seen from the FIG. 9 that the manual hot start generated a well amplified correct product whereas the bench start generated the product of the incorrect size. The two reactions that excluded either ammonium sulfate or both Tris and ammonium sulfate generated the amplification products, however the amplification was not as optimal as when both Tris and ammonium sulfate are also provided in the buffer during the precipitate formation.

Example 9
Concentration Curve of Ammonium Phosphate in Magnesium Precipitate Hot Start Reactions

Figure 10:
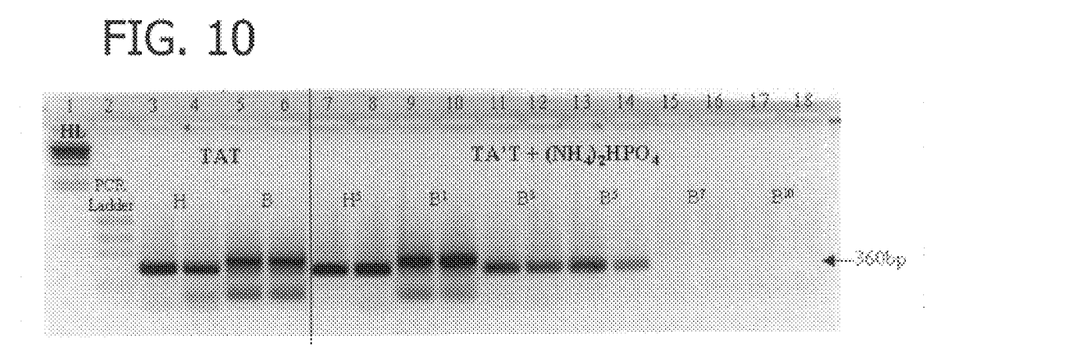
FIG. 10 is an image of an agarose gel depicting the optimal concentration of ammonium phosphate (($NH_4)_2HPO_4$) for use in the magnesium precipitate hot start PCR reactions. All lanes show the amplification of *Cryptosporidium parvum* heat shock protein homolog gene (hsp70). Lanes 1 and 2 represent the standard molecular markers. Lanes 3 and 4 and lanes 5 and 6 represent the manual hot start and the bench start, respectively. As shown in lanes 7 and 8, the manual hot start was also performed with TAT buffer containing ammonium phosphate as the source of phosphate ions. The remaining lanes (9–18) depict the amplification products in magnesium precipitate hot start reactions that utilized ammonium phosphate. In these reactions, only the concentration of phosphate ions was increased while the concentration of ammonium ions was kept constant. The concentrations of phosphate that were tested are represented by superscripts and include: 1 mM (lanes 9 and 10), 3 mM (lanes 11 and 12), 5 mM (lanes 13 and 14), 7 mM (lanes 15 and 16), and 10 mM (lanes 17 and 18).

*Cryptosporidium parvum* heat shock protein homolog gene (hsp70) was amplified using the following PCR program: 68° C. for 3 minutes, followed by 42 cycles of 95° C. for 40 seconds, 58° C. for 1 minute, and 68° C. for 2 minutes, and the results are shown in FIG. 10. The primers used to amplify this gene were:

CPHSPT2F: TCCTCTGCCGTACAGGATCTCTTA (SEQ. ID. NO. 5) and

CPHSPT2R: TGCTGCTCTTACCAGTACTCTTATCA (SEQ. ID. NO. 6).

See Di Giovanni et al., "Real Time Quantitative PCR Detection of Intact and Infectious *Cryptosporidium parvum* Oocysts for Water Industry Applications", Abstracts of the 100th General Meeting of the American Society for Microbiology, 2000.

The mastermix consisted of:

10 mM each DNTP (0.5 ul each dNTP/rxn)

10 uM CPHSPT2F (1 ul/rxn)

10 uM CPHSPT2R (1 ul/rxn)

1 pg/ul *Cryptosporidium parvum* DNA (0.1 ul/rxn)

200 ng/ul denatured Calf Thymus DNA (2 ul/rxn)

Klentaq1 Mix (5 ul/rxn), and sufficient volume of dH$_2$O so that the total volume of the reaction is 50 ul.

The manual hot start and the bench start reactions were performed as in the previous examples. H[5] denotes the manual hot start reaction, wherein the TAT buffer contained 5 mM ammonium phosphate ((NH$_4$)$_2$HPO$_4$) as the source of phosphate ions. In the magnesium precipitate hot start reactions, the amount of ammonium phosphate was varied in such way that only the phosphate concentration was effectively changed. The concentration of ammonium ions was kept constant by decreasing the amount of ammonium sulfate in the TAT buffer. The TAT buffers modified in this manner are marked in the FIG. 10 as TA'T. All the modified buffers had the same pH of 9.2.

As can be seen from FIG. 10, both forms of manual hot start worked well with or without ammonium phosphate (H[5] and H, respectively) whereas the bench start without ammonium phosphate resulted in the amplification of two incorrect bands. The same incorrect bands were observed in the magnesium precipitate hot start method with 1 mM ammonium phosphate. However, 3 mM and 5 mM concentrations of ammonium phosphate in magnesium precipitate hot start reactions gave rise to significant product amplification. Therefore, ammonium phosphate can successfully be applied in magnesium precipitate hot start PCR as a source of phosphate ions. Furthermore, ammonium phosphate possesses a different range of phosphate concentrations at which magnesium precipitate hot start is functional compared to the phosphoric acid. The ability to use different effective concentration ranges of different phosphate containing compounds allows for broad application of magnesium precipitate hot start method in PCR reactions. These ranges of concentrations can be determined by a skilled artisan using the methods disclosed herein.

It is to be understood that the present invention has been described in detail by way of illustration and example in order to acquaint others skilled in the art with the invention, its principles, and its practical application. Further, the specific embodiments of the present invention as set forth are not intended as being exhaustive or limiting of the invention, and that many alternatives, modifications, and variations will be apparent to those skilled in the art in light of the foregoing examples and detailed description. Accordingly, this invention is intended to embrace all such alternatives, modifications, and variations that fall within the spirit and scope of the following claims. While some of the examples and descriptions above include some conclusions about the way the invention may function, the inventors do not intend to be bound by those conclusions and functions, but puts them forth only as possible explanations.

We claim:

1. A process for synthesizing a nucleic acid extension product, said process comprising:
   a. forming or obtaining a reagent comprising a source of magnesium ions and a source of phosphate ions, wherein the source of magnesium ions and the source of phosphate ions form a precipitate at a temperature below 34° C.;
   b. making a mixture comprising the reagent of step (a), wherein said magnesium ions are contained in said precipitate a DNA polymerase, deoxyribonucleoside triphosphates, primers and a target nucleic acid sequence;
   c. releasing the magnesium ions from the precipitate at a temperature above 34° C. thereby activating the DNA polymerase;
   d. if the nucleic acid is double stranded, separating the strands and denaturing intrastrand structures;
   e. annealing the primers to the target nucleic acid sequence at an appropriate temperature; and
   f. synthesizing an extension product of each primer using the activated DNA polymerase, wherein the primer extension product is complementary to the target nucleic acid DNA strand.

2. The process of claim 1 further comprising:
   g. separating the primer extension products from the templates on which they are synthesized to produce single-stranded molecules; and
   h. repeating steps (f) and (g) at least once.

3. The process of claim 1, wherein the precipitate comprises magnesium and phosphate.

4. The process of claim 3, wherein the reagent further comprises ammonium sulfate and Tris(hydroxymethyl) aminomethane.

5. The process of claim 1, wherein the magnesium ions are released from the precipitate in step (c) by heating the mixture to alternating temperatures within the range of between 50° C. and 95° C.

6. The process of claim 1 wherein the source of phosphate ions in the reagent comprises phosphoric acid, potassium phosphate or ammonium phosphate.

7. The process of claim 6 wherein the reagent comprises phosphoric acid at a concentration of about 3 to 13 mM.

8. The process of claim 6 wherein the reagent comprises ammonium phosphate at a concentration of about 2 to 6 mM.

9. The process of claim 6 wherein the reagent has a pH above 7.

10. The process of claim 6 wherein the reagent further comprises Tris at a concentration of about 50 mM.

11. The process of claim 6 wherein the reagent further comprises ammonium sulfate at a concentration of about 16 mM.

12. The process of claim 1 wherein the source of magnesium ions in the reagent comprises magnesium chloride, magnesium hydroxide, magnesium carbonate or magnesium sulfate.

13. The process of claim 1 wherein if the target nucleic acid sequence is a RNA sequence, first reverse transcribing the RNA into cDNA.

14. The process of claim 1 wherein the DNA polymerase is TaqLA, KlentaqLA or Klentaq1.

15. The process of claim 14 wherein the source of phosphate ions is phosphoric acid and the source of magnesium ions is magnesium chloride.

16. The process of claim 14 wherein the magnesium ions are released from the precipitate in step (c) by heating the mixture to alternating temperatures within the range of between 50° C. and 95° C.

* * * * *

UNITED STATES PATENT AND TRADEMARK OFFICE
CERTIFICATE OF CORRECTION

PATENT NO. : 6,403,341 B1
DATED : June 11, 2002
INVENTOR(S) : Barnes, Wayne M. et al.

It is certified that error appears in the above-identified patent and that said Letters Patent is hereby corrected as shown below:

<u>Title page,</u>
Item [75], Inventors, please replace "Katherine R. Rowlyk's" address of
"St. Louis, MO (US)" with -- 1115 Sir Francis Drake Blvd., Apt. 16, Kentfield, CA (US) 94904 --

<u>Column 2,</u>
Lines 56 and 61, add a space between "1X" and "buffer"

<u>Column 8,</u>
Line 30, add a space between "±" and "one"

<u>Column 10,</u>
Line 2, after "30°", add -- C --

<u>Column 11,</u>
Line 56, remove space between "Klentaq-278" and ";"

<u>Column 12,</u>
Lines 46, 48 and 61, "in vivo" should be italicized
Line 50, "in situ" should be italicized <u>Column 13,</u>
Line 3, replace "CDNA" with -- cDNA --
Line 29, replace "oxyribonuclotide" with -- oxyribonucleotide --

<u>Column 14,</u>
Line 34, add a space between "ul)" and "for"

<u>Column 17,</u>
Line 32, replace "4*a*" with -- 4A -- and "4*b*" with -- 4B --

UNITED STATES PATENT AND TRADEMARK OFFICE
CERTIFICATE OF CORRECTION

PATENT NO.    : 6,403,341 B1
DATED         : June 11, 2002
INVENTOR(S)   : Barnes, Wayne M. et al.

It is certified that error appears in the above-identified patent and that said Letters Patent is hereby corrected as shown below:

<u>Column 18,</u>
Line 30, replace "DNTP" with -- dNTP --

Signed and Sealed this

Eleventh Day of February, 2003

JAMES E. ROGAN
*Director of the United States Patent and Trademark Office*